United States Patent [19]
Jones et al.

[11] Patent Number: 5,922,312
[45] Date of Patent: Jul. 13, 1999

[54] HAIR COSMETIC COMPOSITIONS

[75] Inventors: Stevan David Jones, Camberley; Philip John Marchant, Egham, both of United Kingdom

[73] Assignee: The Procter & Gamble Company, Cincinnati, Ohio

[21] Appl. No.: 08/776,453

[22] PCT Filed: Jun. 30, 1995

[86] PCT No.: PCT/US95/08336

§ 371 Date: Apr. 3, 1997

§ 102(e) Date: Apr. 3, 1997

[87] PCT Pub. No.: WO96/03967

PCT Pub. Date: Feb. 15, 1996

[30] Foreign Application Priority Data

Jul. 29, 1994 [GB] United Kingdom .................. 9415324

[51] Int. Cl.$^6$ ................................ A61K 7/11; A61K 7/06
[52] U.S. Cl. ..................................... 424/70.13; 424/70.17; 424/70.11; 424/DIG. 2
[58] Field of Search ............................ 424/70.11, 70.17, 424/70.13, DIG. 2

[56] References Cited

U.S. PATENT DOCUMENTS

| | | | |
|---|---|---|---|
| 5,066,481 | 11/1991 | Helioff | 424/47 |
| 5,118,498 | 6/1992 | Helioff et al. | 424/70 |
| 5,194,260 | 3/1993 | Grollier | 424/401 |
| 5,304,334 | 4/1994 | Lahanas | 242/314 |
| 5,362,789 | 11/1994 | Kwak | 524/401 |

*Primary Examiner*—Sally Gardner-Lane
*Attorney, Agent, or Firm*—Tara M. Rosnell; Darryl C. Little

[57] ABSTRACT

A hair care composition comprising: (a) from about 0.01 to about 3% by weight of gelling agent comprising a copolymer of methyl vinyl ether/maleic anhydride, cross-linked with $C_4$–$C_{16}$ alkadiene of hydrolysis products thereof; (b) from about 0.1% to about 10% by weight of hair fixative copolymer comprising a cationic copolymer of nonionic cellulose and diallyl dimethyl ammonium chloride; and the balance comprising a carrier suitable for application to hair. The liquid hair cosmetic products have an improved non-tacky on-hair and on-hand feel, demonstrate excellent hair styling benefits in addition to ease of brush-out.

19 Claims, No Drawings

HAIR COSMETIC COMPOSITIONS

TECHNICAL FIELD

The present invention relates to hair cosmetic compositions. More particularly, this invention relates to hair cosmetic compositions containing a gelling agent and a hair fixative/conditioning polymer and having improved "in-use" and "on-hair" feel properties in addition to manageability and style retention benefits.

BACKGROUND OF THE INVENTION

The desire to have the hair retain a particular shape is widely held. A common methodology for accomplishing this is applying hair styling, or "setting" compositions to the hair, typically to damp or dry hair. These compositions provide temporary setting benefits, and should be removable by water and/or by shampooing. The materials used in the compositions to provide the setting benefits are generally applied in the form of mousses, gels, lotions or sprays.

High levels of style retention, or hold, are typically expected from hair compositions whether applied as a gel or a spray. Style retention in gel products is typically achieved by use of one or more hair fixative polymers, such as polyvinylpyrollidone (PVP) and the copolymer of PVP with vinyl acetate (PVP/VA) in combination with a gelling agent. A commonly used gelling agent is crosslinked polyacrylic acid, known by the CTFA name of Carbomer. When such polymers are incorporated into hair fixative compositions containing conventional gelling agents they can provide suitable style retention attributes. However, such compositions can give a sticky feel on the hair and hands during and after application as well as leaving the hair feeling stiff and unnatural.

It has now been found that certain combinations of gelling agents and hair fixative polymers can deliver excellent styling benefits without the sticky and stiff feel usually associated with conventional styling gels.

Thus a need exists for hair styling compositions which deliver effective style retention, impart a hair conditioning effect, have a non-sticky hair and on-hand feel, are easily brushed out, are resistant to flakiness and at the same time have stable product and viscosity characteristics and remain fully stable under long term and stressed temperature storage.

SUMMARY OF THE INVENTION

According to one aspect of the invention, there is provided a hair cosmetic composition comprising:
(a) from about 0.01% to about 3% by weight of gelling agent comprising a copolymer of methyl vinyl ether/maleic anhydride, crosslinked with $C_4$–$C_{16}$ alkadiene or hydrolysis products thereof;
(b) from about 0.1% to about 10% by weight of hair fixative polymer comprising a cationic copolymer of nonionic cellulose and diallyl dimethyl ammonium chloride; and
(c) the balance comprising a carrier suitable for application to hair.

The essential, as well as the optional, components of the present invention are described below. All levels and ratios are on a weight basis unless otherwise specified.

Gelling Agent

The compositions of the present invention contain from about 0.01% to about 3% preferably from about 0.05% to about 2%, more preferably from about 0.5% to about 1.5%, most preferably from about 0.6% to about 1% by weight of gelling agent. It is this gelling agent which in combination with a cationic hair fixative polymer imparts hair setting and conditioning benefits without the tacky dry-hair feel and on-hand stickiness normally associated with hair styling cosmetics. The gelling agents suitable for use in the present invention comprise a copolymer of methyl vinyl ether/maleic anhydride, and hydrolysis products thereof, crosslinked with $C_4$–$C_{16}$, preferably $C_6$–$C_{12}$, more preferably $C_8$–$C_{10}$ alkadiene. The gelling agents typically have a viscosity in the region of from about 50,000 cps to about 150,000 cps, preferably from about 70,000 cps to about 100,000 cps (measured as 0.5% gelling agent in nonalcoholic solution at pH7; Brookfield RVT, Spindle TE, 10 rpm).

In its broadest aspect, the copolymer utilised in the present application comprise a copolymer of methyl vinyl ether/maleic anhydride (hereafter identified as A) crosslinked with $C_4$–$C_{16}$, preferably $C_6$–$C_{12}$, more preferably $C_8$–$C_{10}$ alkadiene (hereafter identified as B). Examples of suitable polymers and their preparations are described in detail in "Polymers and Thickeners" Vol. 108, May 1993, p61–67, S. L. Kopolow, Y. T. Kwak and M. Helioff. These polymers comprise part A and B as defined above. In preferred embodiments, B comprises $C_6$–$C_{14}$ alkadiene, more preferably a $C_6$–$C_{12}$ alkadiene, most preferably a $C_8$–$C_{10}$ alkadiene.

The preferred gelling agent for use herein is methyl vinyl ether/maleic anhydride, crosslinked with 1,9-decadiene (PVM/MA decadiene crosspolymer), available from ISP as Stabileze 06 (RTM).

The hair gelling agents, herein are preferably utilised in at least partially neutralised form in order to obtain the required gel structure and overall pH of the hair cosmetic compositions.

The gelling agent can be neutralised to a level of from about 30% to about 100%, preferably from about 40% to about 98%, more preferably from about 50% to about 95% with base. Any conventionally used base, organic or inorganic, may be used for neutralisation of the acidic gelling agents. Hydroxides of alkali and alkaline earth metals and amino alcohols are suitable neutralisers for use in the present hair cosmetic compositions.

Examples of suitable organic neutralising agents which may be included in the hair cosmetic compositions of the present invention include amines, especially amino alcohols such as 2-amino-2-methyl-1,3-propanediol (AMPD), 2-amine-2-ethyl-1,3-propanediol (AEPD), 2-amino-2-methyl-1-propanol (AMP), 2-amino-1-butanol (AB), monethanolamine (MEA), diethanolamine (DEA), triethanolamine (TEA), monoisopropanolamine (MIPA), diisopropanolamine (DIPA), triisopropanolamine (TIPA), dimethyl steramine (DMS) and amino methyl propanol (AMP) and mixtures thereof.

Preferred neutralising agents for use in compositions of the present invention are potassium and sodium hydroxides, aminomethyl propanol (AMP) and triethanolamine (TEA) and mixtures thereof.

In addition to the specific gelling agents as detailed supra such compositions may optionally include an auxiliary gelling agent at from about 0.01% to about 1%, preferqably from about 0.1% to about 0.5% by weight. Suitable auxiliary gelling agents can be selected from any conventional gelling agent such as a crosslinked polyacrylic acid copolymer, ethylene maleic anhydride copolymers or hydroxyethylcellulose and its derivatives. The preferred auxiliary gelling for use herein is hydroxyethylcellulose.

Carrier

The hair cosmetic compositions of the present invention also include a carrier which can be aqueouse or non-aqueous and mixtures thereof. This can comprise any of those conventionally used in polymer containing hair cosmetic formulations. The carrier is generally present in the hair cosmetic compositions at from about 70% to about 99.89%, preferably from about 78% to about 99.5% by weight. More preferably, the carrier is present at from about 80% to about 99% by weight of the total composition.

Organic solvents suitable for use in the carrier in compositions according to the present invention include $C_1$–$C_6$ alkanols, carbitol, acetone and mixtures thereof. $C_1$–$C_6$ alkanols preferred for use in the present compositions are $C_2$–$C_4$ monohydric alcohols such as ethanol, isopropanol and mixtures thereof.

The preferred hair compositions according to the present invention contain from 70% to about 99.89% by weight of water, preferably from 78% to about 99.5%, more preferably from about 80% to about 99% by weight of water as the carrier.

Cationic Hair Fixative Polymer

In addition to the gelling agent the compositions according to the present invention comprise, as a second essential component, a hair fixative polymer. This hair fixative polymer is preferably solubilized or colloidally dispersed in the hair cosmetic carrier along with the gelling agent copolymer.

The preferred hair fixative polymer component of the hair cosmetic compositions of the present invention comprises a cationic copolymer of hydroxyethyl cellulose and diallyl dimethyl ammonium chloride which is known by the CTFA name Polyquaternium 4 and marketed under the trade names Celquat L200 (RTM) and Celquat H100 (RTM) by National Starch and Chemical Ltd.

The hair fixative polymer is present in an amount of from about 0.1% to about 10%, preferably from about 0.3% to about 8%, more preferably from about 0.5% to about 6%, most preferably from about 0.8% to about 3% by weight of composition. In compositions according to the present invention the weight ratio of gelling agent: hair fixative polymer is in the range of from about 10:1 to about 1:10.

Other hair fixative polymers suitable for use herein in conjunction with the above material include any polymer which is soluble or colloidally dispersible in the hair cosmetic carrier. Solubility and dispersibility are determined at ambient conditions of temperature and pressure (25° C. and at 101.3 kPa (1 Atm)). Such copolymers may be cationic or nonionic in character. Copolymers suitable for use herein have a molecular weight in the range of from about 1,000 to about 5,000,000, preferably from about 50,000 to about 4,000,000, more preferably from about 100,000 to about 3,000,000, most preferably from about 500,000 to about 2,000,000.

In addition cationic and nonionic resins may be utilised as detailed below. Polycationic hair conditioning polymer resins suitable for use herein are described below. For convenience in describing the polymers hereof, monomeric units present in the polymers may be referred to as the monomers from which they can be derived. The cationic monomers can be derived from polymerizable cationic starting monomers, or from polymerizable nonionic monomers which are modified subsequent to polymerization to be of cationic character.

These cationic unsaturated monomers can be polymerized in cationic form, or as an alternative they can be polymerized in-the form of their precursors, which are then modified to be cationic, for example, by a quaternizing agent (eg. ethyl monochloroacetate, diemethyl sulfate, etc.). Preferred cationic monomers include dimethylaminoethyl methacrylate, quaternized dimethylaminoethyl methacrylate, diallyldimethyl ammonium chloride, vinylimidazolium quaternary ammonium monomers and mixtures thereof.

Respresentative examples of nonionic monomers are acrylic or methacrylic acid esters of C1–C24 alcohols, such as methanol, ethanol, 1-propanol, 2-propanol, 1-butanol, 2-methyl-1-propanol, 1-pentanol, 2-pentanol, 3-pentanol, 2-methyl-1-butanol, 1-methyl-1-butanol, 3-methyl-1-butanol, 1-methyl-1-pentanol, 2-methyl-1-pentanol, 3-methyl-1-pentanol, t-butaonl, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol, 1-hexadecanol, 1-octadecanol, and the like, the alcohols having from about 1–24 preferably from about 4–18, more preferably from about 4–12 carbon atoms; styrene; chlorostyrene; vinyl estes such as vinyl acetate; vinyl chloride; vinylidene chloride; acrylonitrile; alpha-methylstyrene; t-butylstyrene; butadiene; cyclohexadiene; ethylene; propylene; vinyl toluene; alkoxyalkyl (meth)acrylate, such as methoxy ethyl (meth)acrylate and butoxytheyl (meth) acrylate; and mixtures thereof. Other nonionic monomers include acrylate and methacrylate derivatives such as allyl acrylate and methacrylate, cyclohexyl acrylate and methacrylate, oleyl acrylate and methacrylate, benzyl acrylate and methacylate, tetrahydrofurfuryl acrylate and methacrylate, ethylene glycol di-acrylate and -methacrylate, 1,3-butyleneglycol di-acrylate and -methacrylate, diacetonacylamide, isobornyl (meth)acrylate, and the like.

Preferred nonionic monomers include n-butyl methacrylate, isobutyl methacrylate, 2-ethylhexyl methacrylate, methyl methacrylate, t-butylacrylate, t-butylmethacrylate, and mixtures thereof.

Representative polar nonionic monomers include acrylamide, N,N-dimethylacrylamide, methacrylamide, N-t-butyl acylamide, methacrylonitrile, acrylamide, acrylate alcohols (eg. C2–C6 acrylate alcohols such as hydroxyethyl acrylate, hydroxyproxyl acrylate), hydroxyethyl methacrylate, hydroxpropyl methacrylate, vinyl pyrrolidone, vinyl ethers, such as methyl vinyl ether, acyl lactones and vinyl pyridine, allyl alcohols, vinyl alcohols and vinyl caprolactam.

Preferred polycationic polymer resins for use herein include cationic guar gum, cationic polysaccharides, homopolymers of dimethyldiallyl ammonium chloride, copolymers of dimethyldiallyl ammonium chloride and acrylamide, cationic amino-functional homopolymers and copolymers derived from acrylic acid and/or methacrylic acid, especially from alkylaminoalkyl acrylate and methacrylate monomers such as dimethylacmonoethyl acrylate and methacrylate, polyalkylene imines and ethoxy polyalkylene imines, vinylimidazolium/vinylpyrrolidone quaternary ammonium copolymers, and mixtures thereof.

The auxilliary hair fixative polymer is incorporated with the Polyquaternium 4 at levels of from about 0.01% to about 10%, preferably from about 0.15 to about 5% by weight. The combination of Polyquat 4 and auxilliary hair fixative polymer is valuable for providing overall hair feel benefits, particularity with respect to flakiness.

The present compositions can be formulated as leave-in hair cosmetic compositions such as gels or creams. Methods of making the hair cosmetic compositions of the present invention are described more specifically in the examples.

The hair cosmetic compositions of the present invention may contain a chelating agent at a level of from about 0.01% to about 5%, preferably from about 0.5% to about 3%, more preferably from about 0.08% to about 1% by weight. Chelating agents suitable for the compositions according to the present invention include salts of ethylenediamine tetraacetic acid including ethylenediamine tetraacetic acid, disodium ethylenediamine tetraacetic acid and pentasodium pentatate. The preferred chelating agent for use in compositions according to the present invention is tetrasodium ethylenediamine tetraacetic acid.

The hair cosmetic compositions of the present invention can also contain a variety of non-essential, optional components such as preservatives, surfactants, block polymers, thickeners and viscosity modifiers, electrolytes, fatty alcohols, pH adjusting agents, perfume oils; UV screening agents; hair conditioning agents, Pearlescants, emollients; lubricants and penetrants such as various lanolin components; protein hydrolysates and other protein derivatives; ethylene adducts and polyoxyethylene cholesterol; volatile and non-volatile silicone fluids. Such conventional optional ingredients are well known to a person skilled in the art, e.g. surfactants used as perfume solubilizing agents such as anionics (e.g., sodium alkyl sulphates, nonionics (amine oxides); amphoterics (aliphatic secondary or tertiary amine derivatives) zwitterionics (aliphatic quaternary ammonium; phosphonium or sulphonium derivatives) and fluorinated surfactants (e.g. Zonyl FSK) (RTM), preferred surfactants for use herein being nonionics such as polyethylene glycol fatty acid esters, isosteareth-20, polysorbate-20, PPG-12-PEG-65 lanolin oil, PEG40 hydrogenated caster oil, polysorbate 80, Oleth-20 and Nonoxynol-10, thickeners and viscosity modifiers such as diethanolamides of long chain fatty acids, sodium chloride, sodium sulphate, and ethyl alcohol; block polymers of ethylene oxide and propylene oxide such as Pluronic (RTM) F88 offered by BASF Wyandotte; preservatives such as DMDM hydantoin, methyl paraben, propyl paraben and diaxolidinyl urea; fatty alcohols such as cetearyl alcohol; electrolyte such as earth and alkaline-earth metal salts; quaternary ammonium ions and cationic amines and halogen ions; pH adjusting agents such as citric acid, succinic acid, sodium hydroxide and triethanolamine; perfiume oils such as Florasynth (RTM) perfumes; hair conditioning agents such as panthenol/pantyl B and pearlescing agents such as ethylene glycol distearate and mica and UV screening agents such as benzophenone-4 and benzophenone-10. Each of these optional materials can be present at a level of from about 0.01% to about 5%, preferably from about 0.05% to about 3%, most preferably from about 0.08% to about 1%, by weight of composition.

The hair cosmetic compositions of the present invention are used in conventional ways to provide the hair styling/holding benefits of the present invention in combination with reduced on-hair and on-hand tack. Such methods can involve applying an effective amount of the product to dry or damp hair before or after the hair is styled, or both. By "effective amount" is meant an amount sufficient to provide the hair volume and style benefits desired considering the length and texture of the hair. The hair cosmetic compositions according to the present invention may be effectively applied to the hair using the hands, using a comb or brush or by applying with a sponge or 'wipe'.

The invention is illustrated by the following non-limiting examples.

Gelling agent—Stablileze 06 (RTM)
Neutralising agent—Triethanolamine (TEA)
Hair fixative polymer A—Polyquaternium 4 (RTM)
Hair fixative polymer B—PVP/VA
Chelating agent—tetra sodium ethylenediamine tetracetic acid EDTA $(Na)_4$

| Examples      | I          | II         | III        |
|---------------|------------|------------|------------|
| Stabileze 06  | 0.6        | 0.4        | 0.3        |
| Carbomer 980/201 | —       | 0.2        | —          |
| TEA           | 0.6        | 0.6        | 0.3        |
| Polyquat 4    | 1.0        | 0.5        | 1.0        |
| PVP/VA        | —          | 0.5        | 0.5        |
| EDTA $(Na)_4$ | 0.1        | 0.1        | 0.1        |
| Ethanol       | —          | —          | 10.0       |
| Water         | To balance | To balance | To balance |

The hair cosmetic formulations are prepared by (a) dispersing the gelling agent(s) into water, allowing sufficient time for hydration of the gelling agent (30 minutes to 1 hour), then partially neutralising the gelling agent with a suitable base and (b) in a separate step, solubilising the fixative polymer(s) in water along with any non-essential optional ingredients and the chelating agent. The premixes (a) and (b) are combined and the resulting mixture is modified to the desired viscosity and pH characteristics using the remainder of the neutralising base.

The above compositions provide effective style retention, deliver a hair conditioning effect with low on-hand and on-hair tack.

We claim:
1. A hair cosmetic composition comprising:
   (a) from about 0.01% to about 3% by weight of gelling agent comprising a copolymer of methyl vinyl ether/maleic anhydride, crosslinked with $C_4$–$C_{16}$ alkadiene or hydrolysis products thereof:
   (b) from about 0.1% to about 10% by weight of hair fixative polymer comprising a cationic copolymer of nonionic cellulose and diallyl dimethyl ammonium chloride; and
   (c) the balance comprising a carrier suitable for application to hair.

2. A hair cosmetic composition according to claim 1 wherein the viscosity of the gelling agent at 25° C. is in the region of from about 70,000 cps to about 100,000 cps (measured as 0.5% gelling agent in non-alcholic solution at pH7; Brookfield RVT, Spindle TE, 10 rpm).

3. A hair cosmetic composition according to claim 1 wherein the gelling agent is neutralized to a level of from about 30% to about 95%, with base.

4. A hair cosmetic composition according to claim 3 wherein the base is selected from alkali metal, alkaline earth metal and ammonium hydroxides, amines and amino alcohols and mixtures thereof and in particular is selected from triethanolamine, sodium hydroxide and mixtures thereof.

5. A hair cosmetic composition according to claim 1 wherein the weight average molecular weight of the cationic copolymer is in the range of from about 1,000 to about 5,000,000.

6. A hair cosmetic composition according to claim 1 wherein the cationic copolymer comprises a copolymer of hydroxy ethyl cellulose and diallyldimethyl ammonium chloride.

7. A hair cosmetic composition according to claim 1 wherein the hair fixative polymer is present at a level of from about 0.5% to about 8%, by weight.

8. A hair cosmetic composition according to claim 1 wherein the weight ratio of gelling agent: hair fixative polymer(s) is in the range of from about 10:1 to about 1:10.

9. A hair cosmetic composition according to claim 1 wherein the carrier system comprises water and optionally organic solvent selected from $C_1$–$C_6$ alkanols, diols, polyols, carbitols, acetone and mixtures thereof.

10. A hair cosmetic composition according to claim 1 wherein the gelling agent copolymer crosslinking agent is an alkadiene selected from $C_4$–$C_{16}$ alkadienes.

11. A hair cosmetic composition according to claim 1 wherein the gelling agent is a copolymer of methyl vinyl ether/maleic anhydride crosslinked with 1,9-decadiene.

12. A hair cosmetic composition according to claim 1 wherein the level of gelling agent is from about 0.6% to about 1.0% by weight.

13. A hair cosmetic composition according to claim 3 wherein the gelling agent is neutralized to a level of from about 40% to about 80% with base.

14. A hair cosmetic composition according to claim 3 wherein the gelling agent is neutralized to a level of from about 50% to about 60% with base.

15. A hair cosmetic composition according to claim 7 wherein the hair fixative polymer is present at a level of from about 0.8% to about 6% by weight.

16. A hair cosmetic composition according to claim 15 wherein the hair fixative polymer is present at a level of from about 1% to about 3% by weight.

17. A hair cosmetic composition according to claim 10 the gelling agent copolymer crosslinking agent is an alkadiene selected from $C_6$–$C_{14}$ alkadienes.

18. A hair cosmetic composition according to claim 17 wherein the gelling agent copolymer crosslinking agent is an alkadiene selected from $C_6$–$C_{12}$ alkadienes.

19. A hair cosmetic composition according to claim 18 wherein the gelling agent copolymer crosslinking agent is an alkadiene selected from $C_8$–$C_{10}$ alkadiene such as 1,9-decadiene.

* * * * *